US00PP19658P2

(12) United States Plant Patent
Heinrich

(10) Patent No.: US PP19,658 P2
(45) Date of Patent: Jan. 27, 2009

(54) ***SCAEVOLA* PLANT NAMED 'WESSCAETOB'**

(50) Latin Name: *Scaevola aemula*
Varietal Denomination: Wesscaetob

(75) Inventor: Westhoff Heinrich, Südlohn (DE)

(73) Assignee: Gartenbau und Spezialkuturen Westhoff GbR, Südlohn (DE)

( * ) Notice: Subject to any disclaimer, the term of this patent is extended or adjusted under 35 U.S.C. 154(b) by 0 days.

(21) Appl. No.: 11/903,539

(22) Filed: Sep. 21, 2007

(51) Int. Cl.
*A01H 5/00* (2006.01)

(52) U.S. Cl. ..... Plt./363

(58) Field of Classification Search ..... Plt./363
See application file for complete search history.

(56) References Cited

PUBLICATIONS

UPOVROM GTITM Plant Variety Database 2008/01, GTI Jouve Retrieval Software, Citation for *Scaevola* 'Wesscaetob', one page.

*Primary Examiner*—Annette H Para
*Assistant Examiner*—June Hwu
(74) *Attorney, Agent, or Firm*—C. A. Whealy

(57) ABSTRACT

A new and distinct cultivar of *Scaevola* plant named 'Wesscaetob', characterized by its compact and mounded plant habit; freely branching habit; freely flowering habit; and violet blue-colored flowers.

1 Drawing Sheet

Botanical designation: *Scaevola aemula.*
Cultivar denomination: 'Wesscaetob'.

BACKGROUND OF THE INVENTION

The present invention relates to a new and distinct cultivar of *Scaevola,* botanically known as *Scaevola aemula,* and hereinafter referred to by the name 'Wesscaetob'.

The new *Scaevola* is a product of a planned breeding program conducted by the Inventor in Südlohn, Germany The objective of the breeding program is to create new compact and freely-flowering *Scaevola* cultivars.

The new *Scaevola* originated from a cross-pollination made by the Inventor in Südlohn, Germany in 2003 of the *Scaevola aemula* cultivar Brilliant, disclosed in U.S. Plant Pat. No. 12,099, as the female, or seed, parent with a proprietary selection of *Scaevola aemula* identified as code number 03P61, not patented, as the male, or pollen, parent. The cultivar Wesscaetob was discovered and selected by the Inventor as a flowering plant within the progeny of the stated cross-pollination in a controlled environment in Südlohn, Germany in 2004.

Asexual reproduction of the new *Scaevola* by terminal cuttings in a controlled environment in Südlohn, Germany since 2004, has shown that the unique features of this new *Scaevola* are stable and reproduced true to type in successive generations.

SUMMARY OF THE INVENTION

The cultivar Wesscaetob has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Wesscaetob'. These characteristics in combination distinguish 'Wesscaetob' as a new and distinct cultivar of *Scaevola:*

1. Compact and mounded plant habit.
2. Freely branching habit.
3. Freely flowering habit.
4. Violet blue-colored flowers.

Plants of the new *Scaevola* can be compared to plants of the female parent, the cultivar Brilliant. Plants of the new *Scaevola* differ from plants of the cultivar Brilliant in the following characteristics:

1. Plants of the new *Scaevola* are more compact than plants of the cultivar Brilliant.
2. Plants of the new *Scaevola* have smaller leaves than plants of the cultivar Brilliant.
3. Plants of the new *Scaevola* have smaller flowers than plants of the cultivar Brilliant.

Plants of the new *Scaevola* can be compared to plants of the male parent selection. Plants of the new *Scaevola* differ from plants of the male parent selection in the following characteristics:

1. Plants of the new *Scaevola* have finer branches than plants of the male parent selection.
2. Plants of the new *Scaevola* have longer leaves than plants of the male parent selection.
3. Plants of the new *Scaevola* have larger flowers than plants of the male parent selection.

Plants of the new *Scaevola* can be compared to plants of the *Scaevola aemula* cultivar Fancy, disclosed in U.S. Plant Pat. No. 9,867. In side-by-side comparisons conducted in S üdlohn, Germany, plants of the new *Scaevola* differed from plants of the cultivar Fancy in the following characteristics:

1. Plants of the new *Scaevola* were more compact and mounding than plants of the cultivar Fancy.
2. Plants of the new *Scaevola* had smaller leaves than plants of the cultivar Fancy.

3. Plants of the new *Scaevola* had smaller flowers than plants of the cultivar Fancy.
4. Flowers of plants of the new *Scaevola* and the cultivar Fancy differed in flower color as flowers of plants of the cultivar Fancy had a white-colored band at the base of the petals.

BRIEF DESCRIPTION OF THE PHOTOGRAPH

The accompanying colored photograph illustrates the overall appearance of the new *Scaevola,* showing the colors as true as it is reasonably possible to obtain in colored reproductions of this type. Colors in the photograph may differ slightly from the color values cited in the detailed botanical description which accurately describe the colors of the new *Scaevola.* The photograph comprises a side perspective view of a typical flowering plant of 'Wesscaetob' grown in a container.

DETAILED BOTANICAL DESCRIPTION

The photographs and following observations, measurements and values describe plants grown in Südlohn, Germany in containers in a glass-covered greenhouse during the summer under conditions which closely approximate commercial production. During the production of the plants, day temperatures ranged from about 20° C. to 25° C., night temperatures ranged from about 16°C. to 18°C. and light levels ranged from about 3,000 lux to about 50,000 lux. Plants were about four months old when the photographs and the description were taken. In the description, color references are made to The Royal Horticultural Society Colour Chart, 2001 Edition, except where general terms of ordinary dictionary significance are used.

Botanical classification: *Scaevola aemula* cultivar Wesscaetob.

Parentage:

*Female, or seed, parent.*—*Scaevola aemula* cultivar Brilliant, disclosed in U.S. Plant Pat. No. 12,099.

*Male or pollen parent.*—Proprietary selection of *Scaevola aemula* identified as code number 03P61, not patented.

Propagation:

*Type.*—By cuttings.

*Time to initiate roots.*—About three to four weeks at 20° C.

*Time to develop roots.*—About four to five weeks at 20° C.

*Root description.*—Fibrous; color, 158A.

*Rooting habit.*—Freely branching; moderately dense to dense.

Plant description:

*Plant form and growth habit.*—Compact and mounded plant habit. Vigorous growth habit.

*Branching habit.*—Freely branching, lateral branches potentially forming at every node.

*Plant height.*—About 13.7 cm.

*Plant diameter* (*area of spread*).—About 30 cm to 50 cm.

Lateral branch description:

*Length.*—About 13 cm to 45 cm.

*Diameter.*—About 4.3 mm.

*Internode length.*—About 1.7 cm to 1.8 cm.

*Texture.*—Smooth.

*Color.*—146A.

Foliage description:

*Arrangement.*—Alternate, simple; sessile.

*Length.*—About 4.3 cm to 6.1 cm.

*Width.*—About 1.7 cm to 2.4 cm.

*Shape.*—Spatulate.

*Apex.*—Acute.

*Base.*—Attenuate.

*Margin.*—Irregularly serrated.

*Texture, upper and lower surfaces.*—Slightly pubescent.

*Venation pattern.*—Pinnate, arcuate.

*Color.*—Developing foliage, upper surface: 147A. Developing foliage, lower surface: 146A. Fully developed foliage, upper surface: 147A; venation, 147A. Fully developed foliage, lower surface: 146B; venation, 144B.

Flower description:

*Flower type and shape.*—Zygomorphic, semi-circular, fan-shaped flowers with five petals fused at the base to form a tubular flower throat. Flower throat open along the upper surface exposing reproductive organs. Flowers not fragrant.

*Flower arrangement and quantity.*—Solitary sessile flowers arise from leaf axils. Flowers face mostly outwardly. Freely flowering habit, typically about six flowers per apical branch.

*Flowering time.*—Plants flower continuously from spring to the autumn in Germany. Flowers typically last about a week days on the plant. Flowers not persistent.

*Flower buds.*—Shape: Lanceolate. Length: About 1.6 cm to 2 cm. Diameter: About 2.5 mm to 3 mm. Color: 144A.

*Flowers.*—Length: About 1.4 cm. Width: About 3.1 cm. Flower throat diameter: About 4 mm. Flower tube length: About 1.1 cm. Flower tube diameter, base: About 2 mm.

*Petals.*—Quantity: Five, fused at base. Shape: Oblanceolate. Apex: Cuspidate. Margin: Entire. Length, above tube: About 1.3 cm. Width, above tube: About 5 mm. Texture, upper and lower surfaces: Smooth. Color: When opening and fully opened, upper surface: 86B; color becoming closer to 86C with development; venation, 86B to 86C. When opening and fully opened, lower surface: 86C; venation, 85C to 85D. Throat: 6C; venation, 166A. Tube: 145C; venation, 187A.

*Sepals.*—Quantity and arrangement: One large and two smaller sepals in a single whorl fused at the base. Length, larger sepal: About 1.3 cm to 1.6 cm. Length, smaller sepals: About 6 mm to 9 mm. Width, larger sepals: About 4 mm to 6 mm. Width, smaller sepals: About 1 mm to 1.5 mm Shape, larger sepal: Elliptic. Shape, smaller sepals: Acicular. Apex, all sepals: Acute. Margin, all sepals: Mostly entire. Texture, upper and lower surfaces: Slightly pubescent. Color, upper and lower surfaces: 147A.

*Peduncles.*—Length: About 8 cm to 18 cm. Diameter: About 2.5 mm. Texture: Smooth. Color: 144A.

*Reproductive organs.*—Androecium: Stamen quantity per flower: About five. Filament length: About 3 mm to 4 mm. Filament color: 165B to 165C. Anther shape: Ovate. Anther length: About 2 mm. Anther diameter: About 1 mm. Anther color: 162C to 162D. Pollen: Scarce. Pollen color: 162C to 162D. Gynoecium: Pistil quantity per flower: One. Pistil length:

About 1.2 cm. Style length: About 1 cm. Style color: 145A to 145B. Stigma shape: Elongate. Stigma color: 145D. Ovary color: 144A.

*Seeds.*—Quantity per flower: One. Length: About 1.5 mm to 2 mm. Diameter: About 1 mm to 1.5 mm. Color: Close to 202A.

Temperature tolerance: Plants of the new *Scaevola* have been observed to tolerate temperatures from about 5° C. about 30° C.

Pathogen/pest resistance: Plants of the new *Scaevola* have not been shown to be resistant to pathogens and pests common to *Scaevola*.

It is claimed:

1. A new and distinct *Scaevola* plant named 'Wesscaetob' as illustrated and described.

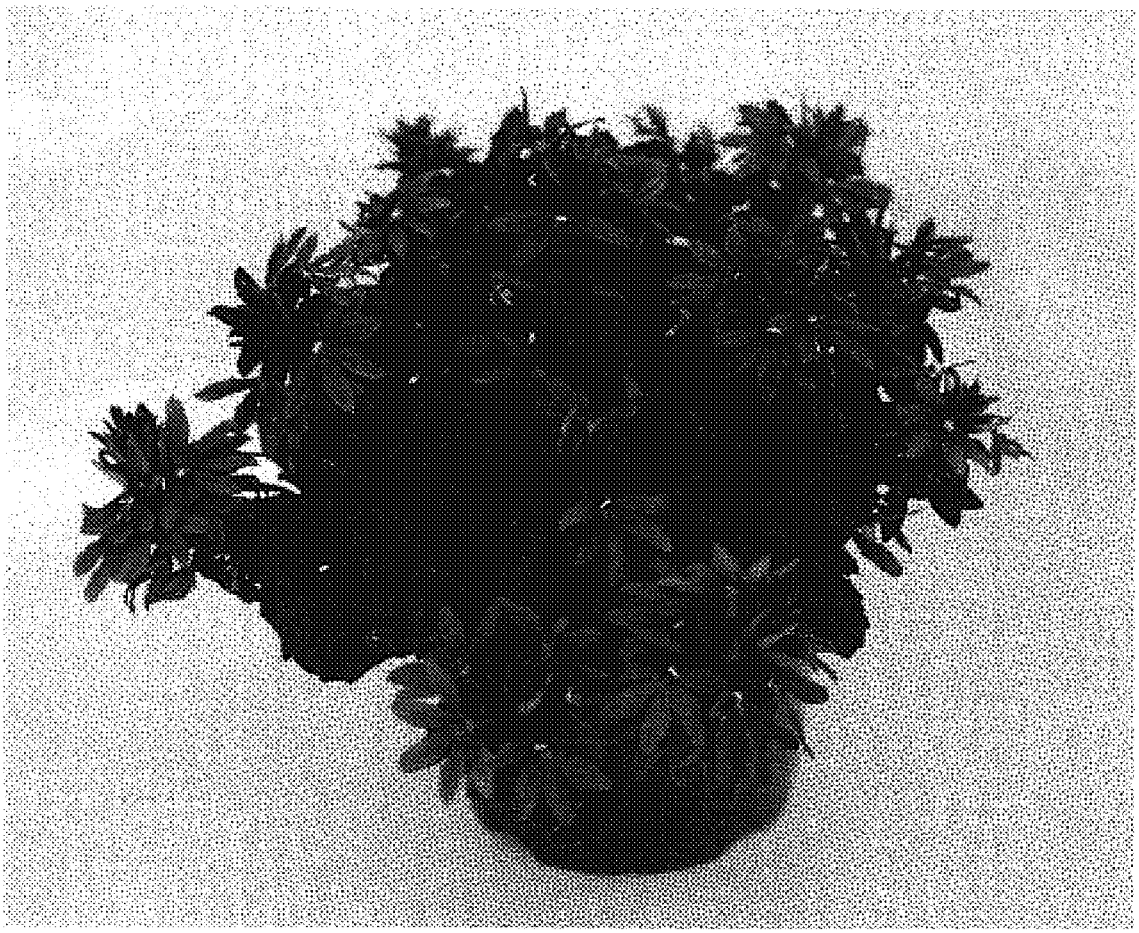

* * * * *